United States Patent [19]

Balkanyi

[11] Patent Number: 5,477,867
[45] Date of Patent: Dec. 26, 1995

[54] DEVICE FOR THE SUPPRESSION OF SNORING

[76] Inventor: Alexander Balkanyi, Morgentalstrasse 31, 8038 Zürich, Switzerland

[21] Appl. No.: 375,525

[22] Filed: Jan. 19, 1995

[30] Foreign Application Priority Data

Feb. 1, 1994 [CH] Switzerland .................. 294/94

[51] Int. Cl.⁶ ............................ A61F 5/56; A61C 5/14
[52] U.S. Cl. ................................. 128/848; 128/859
[58] Field of Search ........................ 128/848, 846, 128/857, 858, 859; 340/575

[56] References Cited

U.S. PATENT DOCUMENTS

| | | | |
|---|---|---|---|
| 3,089,130 | 5/1963 | Wilson | 340/575 |
| 4,220,142 | 9/1980 | Rosen | 340/575 |
| 4,440,160 | 4/1984 | Fischell | 128/857 |
| 4,644,330 | 2/1987 | Dowling | 340/575 |
| 4,788,533 | 11/1988 | Meguignon | 340/575 |
| 4,848,360 | 7/1989 | Palsgard | 340/575 |

FOREIGN PATENT DOCUMENTS

| | | |
|---|---|---|
| 0145160A3 | 6/1985 | European Pat. Off. . |
| 2618327A1 | 1/1989 | France . |
| 30183336 | 11/1981 | Germany ................ 128/848 |
| 3719074A1 | 12/1988 | Germany . |
| WO90/11585 | 10/1990 | WIPO . |

*Primary Examiner*—Michael A. Brown
*Attorney, Agent, or Firm*—Marshall, O'Toole, Gerstein, Murray & Borun

[57] ABSTRACT

The device has a microphone with a combined amplifier, filter and demodulator for detection of snoring noises. If the sleeper is found to be snoring, a control operates a tone generator, which drives a sound emitter via an amplifier for emitting acoustic signals. The individual signals have different frequency distributions and become increasingly unpleasant while the snoring phase lasts. By varying the frequency distribution of the signals, i.e. their pitch, contribution of harmonics, and time modulation, a habituation is prevented. In operation, the control preferably determines which signals have a strong and which signals a weak effect.

13 Claims, 2 Drawing Sheets 5,477,867

DEVICE FOR THE SUPPRESSION OF SNORING

BACKGROUND OF THE INVENTION

1. Field of the Invention

The invention relates to a device for the suppression of snoring by means of the generation of acoustic signals upon the detection of snoring noises.

2. Description of the Prior Art

Various devices for the suppression of snoring have been proposed. Some of them, such as the one described in EP-A-145 160, emit an acoustic signal when the sound of snoring is detected. As, however, the snoring person becomes accustomed to this signal, its volume and duration has to be increased with time. In the device of EP-A-145 160 a counter is provided for this purpose, which counts consecutive snoring noises. The higher its count, the louder and/or longer the signals will be. A sleeper accustomed to this device needs very loud and strong signals before he/she stops snoring. This can lead to hearing damage as well as to an undesirable disturbance of the surroundings. To prevent this, the volume and duration of the signals must be limited. It is, however, very difficult to find a maximum volume that guarantees that the snoring person reacts to it while the danger of hearing damage and/or disturbance of the surroundings is eliminated.

SUMMARY OF THE INVENTION

It is therefore an object to provide a device of the kind mentioned above that does not have these disadvantages. In particular, it should prevent a snoring person from becoming accustomed to the signals without making it necessary to use exceedingly loud signals.

Now, in order to implement these and still further objects of the invention, which will become more readily apparent as the description proceeds, the device for the suppression of snoring is manifested by the features that it comprises a snoring detector for detecting snoring noises, a sound generator being capable of generating a plurality of acoustic signals having differing spectral composition, and a control means for automatically selecting a succession of said sounds upon detection of snoring noises.

By using signals of different spectral composition (i.e. signals having different Fourier spectra), a habituation can be avoided. It is e.g. possible to use tones having different pitch. Preferably, the sounds should become increasingly unpleasant as the snoring continues, e.g. by increasing the intensity of spectral components of higher frequency.

The spectral composition of the signals can also by selected and/or varied in time by using a random mechanism, which will make habituation even more difficult.

Preferably the device is incorporated into a headband, i.e. an elastic band extending around the upper part and the forehead of the sleeper's head. The headband carries a microphone and is connected to an earphone. Such a device is comfortable to wear and does not disturb the sleeper. Instead of using an earphone, the sound emitter can also be incorporated into the headband and transmit its sound directly to the sleeper's cranium. In this case, all components can be integrated in the headband such that no cables are required and the device provides maximum comfort.

The microphone can also be a throat microphone.

If the microphone is carried on any part of the body, it can detect snoring noises transmitted over bones and/or body tissue.

BRIEF DESCRIPTION OF THE DRAWINGS

The invention will be better understood and objects other than those set forth above will become apparent when consideration is given to the following detailed description thereof. Such description makes reference to the annexed drawings, wherein.

DESCRIPTION OF THE PREFERRED EMBODIMENTS

Figure 1:
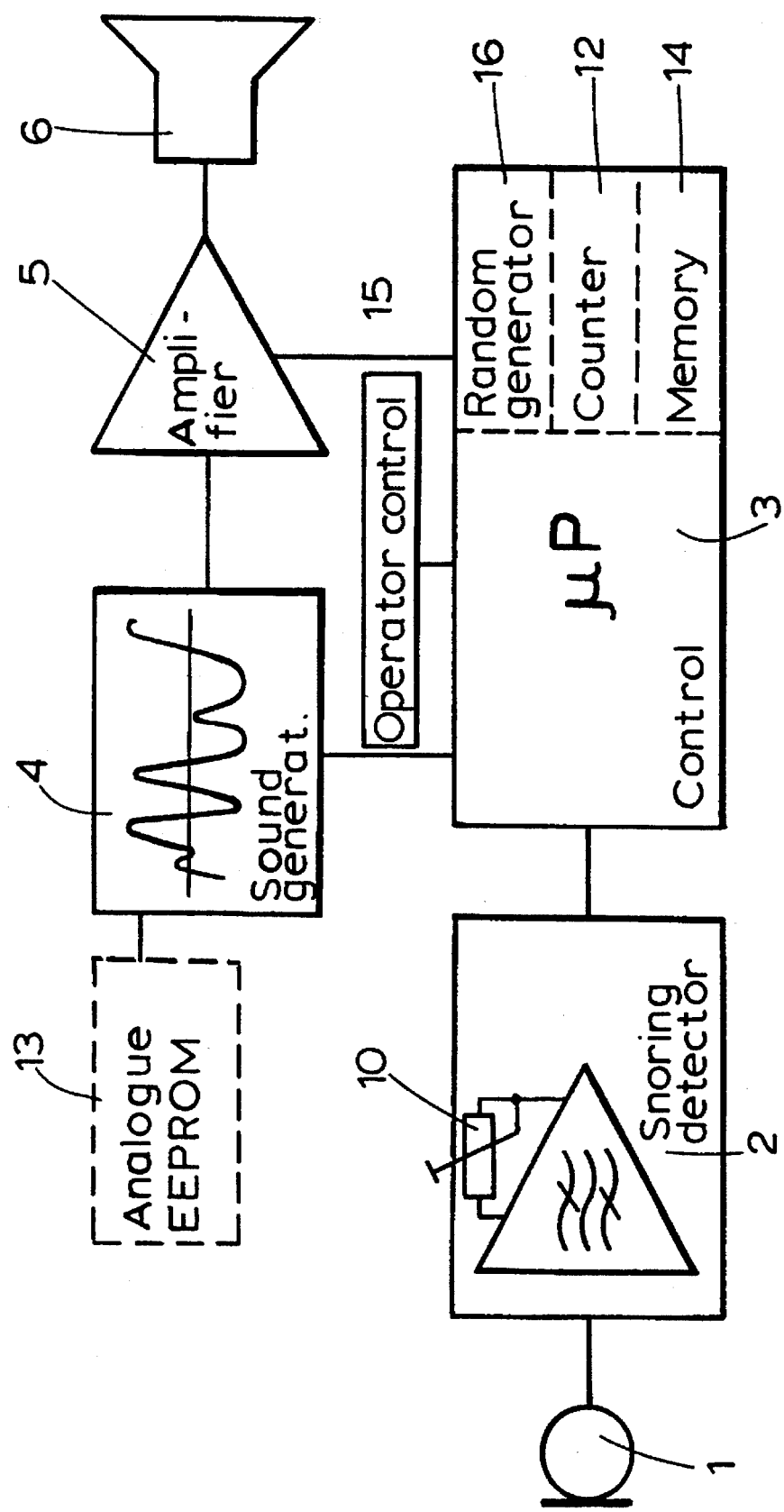
FIG. 1 is a block diagram of the device.

FIG. 1 shows a block diagram of a preferred embodiment of the invention. Microphone 1 detects snoring. Its signal is analyzed in a snoring detector 2 comprising an amplifier, filter and demodulator. A suitable design of this part of the device is e.g. described in EP-A-145160 and the references cited therein.

The signal obtained in this way is fed to control 3. This control is preferably a suitable programmed microprocessor system.

The control drives a sound generator 4 and an amplifier 5. The sound generator 4 is preferably a programmable unit generating audio signals, such as it is known to a person skilled in the art. The sound generator can, however, also be part of the microprocessor system of control 3, in which case the microprocessor can generate the signals e.g. directly by using a digital-analogue converter.

The volume of the signal can be set by controlling the amplifier 5.

The output signal of amplifier 5 is fed to a signal emitter 6, which is preferably a conventional electrodymanic or piezoelectric loudspeaker or earphone.

The device can be assembled in various forms. It can e.g. be designed as a table unit, in which case all components would be integrated into a housing, which could e.g. be placed on the bedside table of the sleeper.

Particularly when the snoring person does not sleep alone, the acoustic signal should not be generated on the bedside table but close to the sleeper, e.g. in his ear or at his forehead or temple. In this case, an arrangement such as described in EP-A-145 160 could be used, where the whole device is a compact unit that fits into the sleeper's ear. It can, however, also be placed behind one's ear. Unfortunately, such a device in or behind the ear is often found to be uncomfortable, especially if the sleeper lies on this ear, thereby also impairing the sound reception of the microphone.

Figure 2:
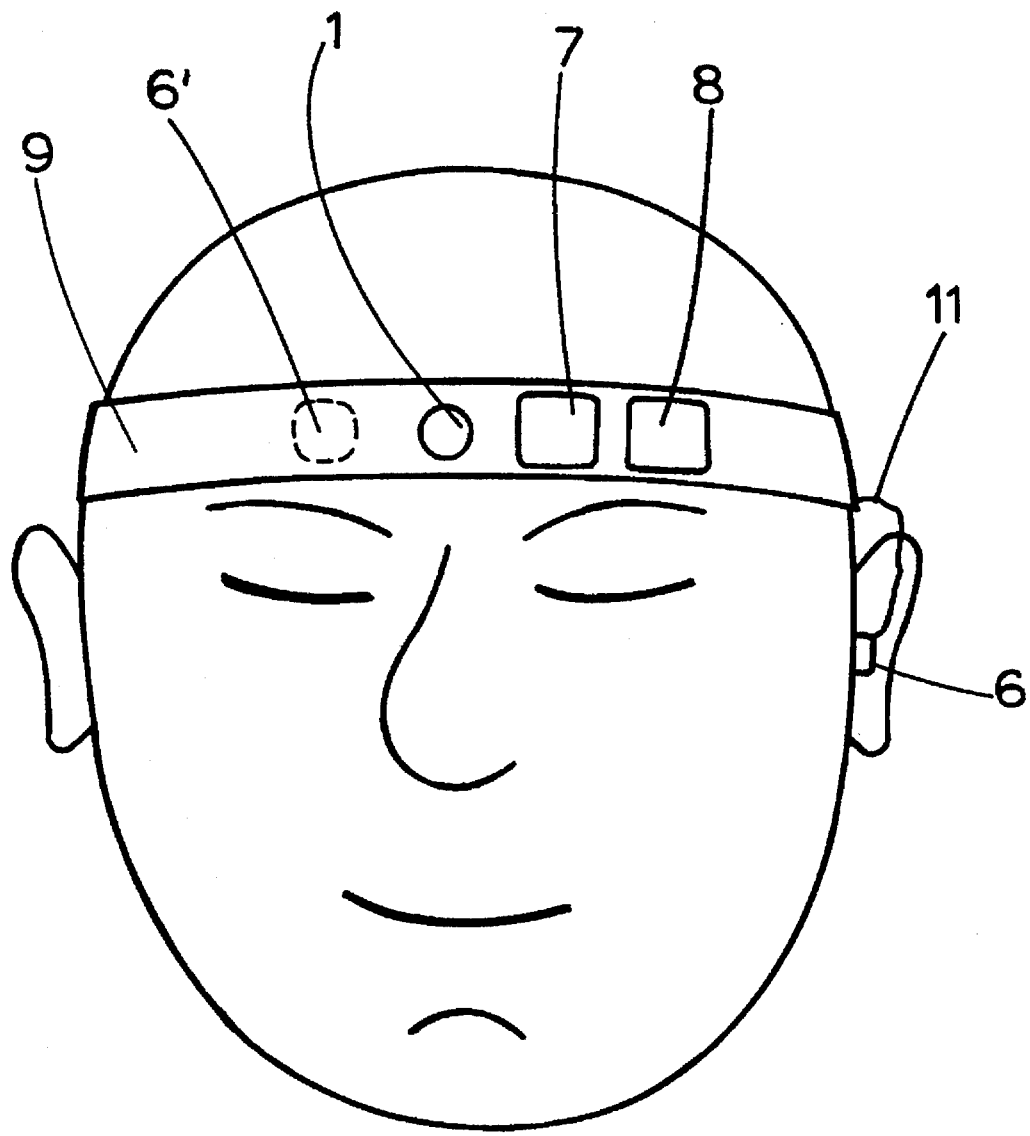
FIG. 2 is a preferred arrangement of the device in a headband.

For these reasons, an arrangement of the device in a headband such as shown in FIG. 2 is preferred. This headband is a soft, elastic band into which the microphone 1, the electronic circuit 7 and a flat battery 8 are incorporated. The microphone is in contact with either the sleeper's forehead or his temple and picks up snoring noises transmitted through the cranium. The sound emitter 6 is fitted into the sleeper's ear and is connected to the electronics 7 by a short cable 11.

Alternatively, the sound emitter can also be a forehead sound emitter 6', in which case it is integrated into the headband 9, and its membrane is directly pressed against the forehead or the temple of the sleeper. In this case, sound transmission again occurs through the cranium, and the signals can hardly be heard by others. In an embodiment with a forehead sound emitter 6', the earphone 6 and its cable 11 are not required. All components are therefore integrated into the headband such that a maximum comfort is achieved and the sleeper can rest in all positions without being disturbed by the device.

In a further preferred embodiment the microphone as fastened to the sleeper's neck by a sticking plaster, preferably close to the larynx and is connected by a cable to the electronics fitted into the ear.

The sensitivity of the microphone can be adjusted by means of a regulator 10 in such a way that only the snoring signals are detected but that other surrounding noises (e.g. the snoring of the partner) do not release a signal.

In operation, the device continually checks if microphone 1 detects a snoring. If no snoring is detected during a pre-defined time interval of e.g. one minute, it is assumed that the sleeper is not snoring and a snoring counter 12 is reset to zero. As soon as a first snoring noise is detected, the snoring counter is incremented by one and a first acoustical signal (signal 1) is emitted. If a second snoring noise is detected during a given time interval after the first snoring noise, it is assumed that the sleeper has snored twice consecutively, the snoring counter is incremented again, and a second acoustic signal (signal 2) is emitted. If a third snoring noise follows within a time interval after the second snoring noise, the snoring counter is incremented again, and a third acoustic signal (signal 3) is emitted, etc. If no further snoring is detected within a time interval after a snoring noise, it is assumed that the sleeper stopped snoring and the snoring phase is over. The snoring counter 12 is reset.

To prevent a habituation to the signals, they become increasingly unpleasant during a snoring phase as the value of counter 12 increases. A comparatively soft and pleasant tone is used for signal 1, e.g. a tone having low frequency and few harmonics. The following signals become more and more efficient, i.e. because their Fourier spectrum is shifted into higher frequency regions or because they become more dissonant. The first few signals can also be completely suppressed such that signal emission e.g. starts only after emission of the third snoring noise.

In a simple embodiment the acoustic signals are constant tones with a fundamental frequency and harmonic frequency components. The fundamental frequency of the first signal is comparatively low in the range of some hundred Hertz and a spectral region where the sensitivity of the ear is not very strong. The fundamental frequency of the following signals increases until it reaches several Kilohertz.

It is also possible to use more complicated signals. Especially, it is e.g. possible to modulate the unpleasant signals in the manner of a siren and/or to use a non-harmonic frequency distribution.

Short sound sequences of various musical instruments or human voices (words) could also be used as signals. They could e.g. be stored in an analogue EEPROM 13 of the tone generator. It would even be possible to play a melody to the snoring person that becomes increasingly discordant as snoring continues.

Signals in the ultrasonic range or with ultrasonic components are also conceivable.

If the snoring person takes a long time to react to the signals, control 3 starts trying various signals. For this purpose, it is provided with a random generator 16 which provides random values for selecting a signal. If snoring stops, control 3 assumes that the most recently played signal has a very strong effect. This signal is stored for use in a later snoring phase. If it is found, however, that the snoring person does not react to a presumably strong, unpleasant signal, it can be assumed that he has become used to it. In this case, the signal will not be used anymore or only be used at the beginning of a snoring phase.

For this purpose, the control is provided with a memory 14 where it is recorded which signals have a strong effect (i.e. they cause the sleeper to stop snoring) and which signals don't.

If the device is equipped with suitable operator controls 15, this memory can also be programmed manually. For this purpose, various signals can be played to the user and he can indicate which signals he finds to be pleasant and which unpleasant.

Since the sound generator 4 can generate e.g. up to 100 different signals and each of these signals can be emitted with various speeds and volumes the device has a sufficiently large "vocabulary" to always be able to find signals to which the sleeper is not accustomed. If an even larger range of signals is required, sound generator 4 or its signal memory 13, respectively, can be designed to be replaceable or even recordable.

Preferably, signals emitted at the beginning of a snoring phase for small values of counter 12 should have a weak effect on the sleeper. The longer the snoring phase lasts and the larger the value of counter 12 becomes, the more effective signals will be used. This results in a gradual increase of the stimulus used on the snoring person. His sleep will become less deep and he will stop snoring before he awakes.

Using the described device habituation is avoided and snoring can be prevented effectively without having to use excessively loud signals.

While there are shown and described presently preferred embodiments of the invention, it is to be distinctly understood that the invention is not limited thereto but may be otherwise variously embodied and practiced within the scope of the following claims.

I claim:

1. A device for the suppression of snoring comprising
    a snoring detector for detecting snoring noises;
    a sound generator being capable of generating a plurality of acoustic signals having differing spectral composition, and
    a control means for automatically selecting a succession of acoustic signals having differing spectral composition upon detection of snoring noises.

2. The device of claim 1, wherein said control means comprises a snoring counter for counting a number of consecutive snoring noises, and wherein selection of said acoustic signals depends on a value of said snoring counter.

3. The device of claim 2, characterized in that spectral components of higher frequency in said spectral composition of the signals in said succession become stronger with an increasing number of consecutively detected snoring noises.

4. The device of claim 1 comprising a random generator for randomly selecting at least part of said acoustic signals.

5. The device of claim 1, wherein said spectral composition of at least part of said signals is modulated in time.

6. The device of claim 1, wherein said spectral composition of each acoustic signal comprises substantially only a fundamental frequency and harmonic frequencies.

7. The device of claim 1, wherein said control means comprises a memory for storing signals the sleeping person reacts strongly to.

8. The device of claim 7, wherein said control means is designed to store in said memory the signal that terminated a snoring phase.

9. The device of claim 1 comprising a headband, wherein said detection means comprises a microphone arranged in said headband.

10. The device of claim 1, wherein said snoring detector comprises a throat microphone.

11. The device of claim 1, wherein said sound generating means comprises a forehead sound emitter.

12. The device of claim 11 comprising a headband, wherein said forehead sound emitter is arranged in said headband.

13. A device for the suppression of snoring comprising a snoring detector for detecting snoring noises, a second generator being capable of generating a plurality of acoustic signals having differing spectral composition and volume, and a control means for automatically selecting a succession of acoustic signals having differing spectral composition and volume upon detection of snoring noises.

* * * * *

UNITED STATES PATENT AND TRADEMARK OFFICE
CERTIFICATE OF CORRECTION

PATENT NO. : 5,477,867
DATED : December 26, 1995
INVENTORS : BALKANYI

It is certified that error appears in the above-identified patent and that said Letters Patent is hereby corrected as shown below:

Column 6, line 2, "a second" should be --a sound--.

Signed and Sealed this

Twenty-seventh Day of August, 1996

Attest:

Attesting Officer

BRUCE LEHMAN

Commissioner of Patents and Trademarks